United States Patent [19]

Sovak et al.

[11] 4,243,653

[45] Jan. 6, 1981

[54] NON-IONIC POLYIODO SUGAR SUBSTITUTED ANILINES

[75] Inventors: Milos Sovak, Rancho Sante Fe; Ramachandra Ranganathan, San Diego, both of Calif.

[73] Assignee: The Regents of the University of California, Berkeley, Calif.

[21] Appl. No.: 34,099

[22] Filed: Apr. 27, 1979

[51] Int. Cl.$^3$ .................... A61K 29/02; C07H 15/18
[52] U.S. Cl. ............................ 424/5; 424/4; 536/18; 536/53; 536/120; 564/158; 564/202; 564/223; 564/441; 564/442; 564/443
[58] Field of Search ................. 424/4, 5; 536/18, 53, 536/120; 260/562 R, 575

[56] References Cited

U.S. PATENT DOCUMENTS

| | | | |
|---|---|---|---|
| 2,951,089 | 8/1960 | Ginsberg et al. | 424/5 |
| 3,076,024 | 1/1963 | Larson | 424/5 |
| 3,701,771 | 10/1972 | Almen et al. | 424/5 |
| 4,109,081 | 8/1978 | Smith | 536/53 |
| 4,125,709 | 11/1978 | Smith | 536/18 |

*Primary Examiner*—Johnnie R. Brown
*Attorney, Agent, or Firm*—Bertram I. Rowland

[57] ABSTRACT

Non-ionic polyiodo saccharidic ether substituted anilines are provided as contrast media, the ether being non-glycosidyl. The compounds have excellent physical properties in having acceptable water solubility or capable of stable suspension, relatively low osmotic pressure, good thermal stability, so as to be heat sterilizable, and a high iodine proportion. The compounds can be prepared from polynitroaromatics by substitution and reduction.

27 Claims, No Drawings

NON-IONIC POLYIODO SUGAR SUBSTITUTED ANILINES

The invention described herein was made in the course of work under a grant from the Department of Health, Education and Welfare.

BACKGROUND OF THE INVENTION

1. Field of the Invention

X-ray contrast media are involved for the visualization of extensive regions of the human body. The contrast agents have to have heavy atoms in high concentration to provide sufficient opacity in the concerned region. Because of the requirement of high concentrations in their use as contrast media, the presence of high proportions of heavy atoms, the desirability of water solubility, and the need for thermal and physiological stability, puts heavy restraints on the type of compounds which may be employed. In addition to the aforementioned restraints, there are concerns with viscosity, osmotic pressure, efficiency of synthesis, and the like.

Numerous iodinated compounds have been prepared for use as contrast media, but in each case, the compounds lack one or more desirable properties. There is, therefore, a continuing effort to develop compounds which provide the best combination of properties for contrast media.

2. Description of the Prior Art

U.S. Pat. No. 3,701,771 describes triiodobenzoyl sugar amines. Compounds which are presently commercially available include bis-3,5-diacetamido benzoate. (Iopamidol), N,N'-di(1',3'-dihydroxypropyl-2') 5-L-lactolylamido isophthaldiamide; and 3-acetamido-5-(N-methyl acetamido) benzoyl derivative of glucosamine. Sovak, et al., Radiology 117:717 (1975) describe di-iodo-triglucosyl benzene. Weitl, et al., J. Med. Chem. 19 353 (1976) describe 2,4,6-triiodo-3-acetamiodo-5-N-methylcarboxamidophenyl $\beta$-D-glucopyranoside as a contrast medium. In the abstracts for the April ACS meeting (1979), is an abstract by Ranganathan and Sovak, entitled "Syntheses of carboxamido-triiodophenyl ethers of hexoses from nitroaromatics and their degradation into pentose derivatives."

SUMMARY OF THE INVENTION

Novel nonionic contrast media are provided which demonstrate a wide variety of desirable properties for contrast media, and are polyiodo non-glycosidyl polyol ether substituted anilines as the aliphatic carboxylic acid amide. The compounds are found to avoid many of the deficiencies of earlier prepared compounds, so far as stability, both thermal and physiologic, while having high iodine content, low osmotic pressure, low toxicity, ease of preparation, and dispersibility or solubility in water. The subject compounds are readily formulated in a wide variety of conventional formulations for injection as contrast media for X-ray examination. The compounds also find use as water soluble high density media.

DESCRIPTION OF THE SPECIFIC EMBODIMENTS

The novel compounds of the subject invention include contrast media and their precursors which are polyol ether substituted polyiodoanilides. The compounds will for the most part have at least 14 carbon atoms and generally not more than 24 carbon atoms, usually not more than 22 carbon atoms, preferably having a ratio of carbon to iodine of not greater than eight to one, preferably not greater than seven to one. There will be three iodine atoms, which are normally separated by two carbon atoms on the benzene ring. The remaining positions will have at least one acylamide group of from one to six, usually two to four carbon atoms, and at least one non-glycosidyl saccharidyl ether group of up to six carbon atoms, generally of from four to six carbon atoms. As precursors, any hydroxylic groups may be present as their ethers, esters, or cycic ethers, where the hydroxyl groups are protected by conventional groups which are readily removable, but provide for stable bonds under the synthetic conditions.

The compounds of this invention will normally have from one to two monosaccharidic ethers linked to a benzene ring through phenolic oxygen. The oxygen of the saccharide will normally be attached to a carbon atom in the one to four position ($\alpha-\delta$), usually the one to three position ($\alpha-\gamma$), preferably the one to two position ($\alpha-\beta$) in relation to the oxo (aldehydo or keto) group of a sugar, preferably at other than a terminal hydroxyl, or at any position of a reduced sugar i.e. polymethylol of from 3 to 6 carbon atoms. By employing these saccharidic ethers, it is found that water solubility can be greatly enhanced for the contrast media, while providing for thermally and physiologically stable linkages, so that water solubility is not diminished during processing and use.

For the most part, the compositions of this invention will have the following formula:

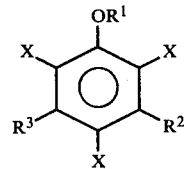

wherein:
the Xs may be the same or different, normally being the same, and are hydrogen or iodine;
$R^1$ is a carbohydrate, a monosaccharidic residue, which includes a reducing sugar i.e. aldose or ketose, or an alditol; when a reducing sugar, the sugar will be bonded to the phenolic oxygen at other than the oxo carbonyl carbon atom, generally at other than a terminal carbon atom, usually one to four, more usually one to three, and preferably from one to two carbon atoms from the oxo carbonyl carbon atom; that is, the sugar is bonded at other than a glycosidic linkage, so that the phenolic oxygen is not part of an acetal or ketal; the carbohydrate will be of up to six carbon atoms, generally being of from three to six carbon atoms, more usually of from five to six carbon atoms, the sugar may be cyclic or acyclic, when cyclic, generally being a furanose or pyranose;
$R^2$ may be nitro, $OR^1$, where the two $R^1$s may be the same or different, usually the same, or $N(R^5)COR^4$;
$R^3$ may be nitro, amino, or $N(R^7)COR^6$;
$R^4$ and $R^6$ may be the same or different, being saturated aliphatic of from one to eight, usually one to six, preferably one to four carbon atoms, wherein the unsubstituted acid group will generally be of from one to four carbon atoms, preferably of from one to three carbon atoms, and more preferably of from two to three carbon atoms, and having from zero to three, usually zero to two, more usually zero to one, oxy substituents, which will be of from zero to four, usually zero to two carbon atoms and includes hydroxyl, alkoxy, and alkylcarboxy (ester), with the proviso that two $R^6$s on different molecules may be taken together to define a linking group to provide a dimer, wherein the two $R^6$S are a bond or a divalent aliphatic linking group of from one to six, usually from two to four carbon atoms, having from zero to two oxy substituents as previously defined; and $R^5$ and $R^7$ may be the same or different, being hydrogen, lower alkyl of from one to three, usually one to two carbon atoms, or lower oxyalkyl of from 2 to 6 usually 2 to 4 carbon atoms having from 0 to 3, usually 0 to 1 oxy substituent of from 0 to 3, usually 0 to 2 carbon atoms, which includes hydroxyl, alkoxy and alkylcarboxy, preferably hydrogen.

Preferably, the compounds of the subject invention are monomers, where the $R^6$s are taken individually.

The contrast media compounds of the subject invention may be broken down into two groups. In the first group, the contrast media compounds have two carbohydrates, usually sugar residues. These compounds will for the most part have the following formula.

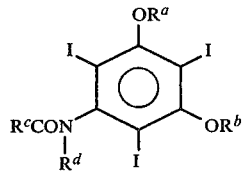

wherein:

I has its normal meaning of iodine;

$R^a$ and $R^b$ may be the same or different, normally being the same, and are carbohydrates of up to six carbon atoms; the monosaccharides are bonded at other than a glycosidyl ether linkage; the monosaccharides will generally be of up to six carbon atoms, usually three to six carbon atoms, more usually five to six carbon atoms and may be acyclic or cyclic, normally forming from five to six membered rings, having one oxygen member (furanosides and pyranosides); the aldoses will normally be linked at carbons two to three, more usually three, while the ketoses will normally be bonded at the three or four positions of the sugar; the alditols will be of from three to six, usually four to six, carbon atoms, and may be bonded at any oxy;

$R^c$ is a substituted or unsubstituted alkyl group, normally being of from one to six, usually of from one to four carbon atoms, when unsubstituted being of from one to three, usually of from two to three carbon atoms having from zero to three, usually zero to two oxy substituents of from zero to two carbon atoms, wherein oxy includes hydroxyl, alkoxy and alkylcarboxy e.g. acetoxy; and $R^d$ is hydrogen, alkyl of from one to two carbon atoms, or oxyalkyl of from 2 to 4 carbon atoms, having 1 to 2 oxy groups including, hydroxyl, alkoxy or alkylcarboxy, with oxygen and nitrogen separated by two carbon atoms, usually hydrogen.

The preferred compounds are those compounds having sugars of from five to six carbon atoms, usually six carbon atoms, and having $R^c$ of from one to two carbon atoms, particularly methyl or ethyl, having from zero to two, preferably zero to one oxy substituent, wherein the oxy substituent is hydroxyl, methoxy or acetoxy.

The carbohydrate residues may be protected or unprotected. Prior to use, the protective group will be removed and will normally be removed during the synthetic procedure. Protective groups include acetals and ketals, such as those formed from oxo-carbonyl compounds, i.e. aldehydes and ketones, the oxo-carbonyl compounds being of from two to seven, usually two to three carbon atoms; esters of aliphatic carboxylic acids of from two to seven carbon atoms and ethers of from one to eight carbon atoms; where all of the groups are readily removable under mild conditions, so as to not disturb the other functionalities present in the molecule. These groups are well known in the art and do not require description or exemplification here.

The other group of compounds is carbohydrate substituted acylated meta-phenylene diamines. These compounds will for the most part have the following formula:

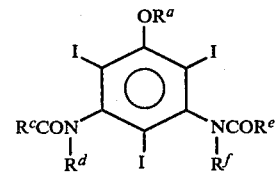

wherein:

I, $R^a$, $R^c$, and $R^d$ have been defined previously;

$R^e$ and $R^c$ may be the same or different, frequently being different, wherein $R^e$ may be unsubstituted, when $R^c$ is substituted, the definition of $R^e$ falling within the definition of $R^c$; and $R^f$ and $R^d$ may be the same or different, wherein $R^f$ will come within the definition of $R^a$, but will preferably be hydrogen or alkyl of from one to two carbon atoms, usually hydrogen.

The carbohydrate substituents as already indicated are monosaccharides or alditols of up to six carbon atoms, usually of from five to six carbon atoms, which are cyclic or acyclic and include such sugars as glucose, fructose, arabinose, ribose, xylose, allose, etc. and alditols as glycerol, threitol, xylitol and mannitol. Conveniently, naturally available sugars will be employed, which may have either the D or L configuration or be racemic mixtures and will be bonded at other than the oxo-carbonyl carbon atom.

The acyl groups may be illustrated by acetyl, glycolyl, methoxyacetyl, lactoyl, DL or D or L, propionyl, or the like. Illustrative compounds of the subject invention include:

TABLE I 3,5-bis(O-D-arabinosyl-2)-2,4,6-triiodopropionanilide

N-methoxyacetyl 3,5-bis(O-D-ribosyl-2)-2,4,6-triiodoaniline

N-hydroxyacetyl 3,5-bis(O-D-galactosyl-3)-2,4,6-triiodoaniline

N-methoxyacetyl 3,5-bis(O-D-mannosyl-3)-2,4,6-triiodoaniline

N-lactoyl 3,5-bis(O-D-talosyl-3)-2,4,6-triiodoaniline

N,N'-dilactoyl 5-(O-D-glucosyl-3)-2,4,6-triiodometaphenylene diamine

N,N'-di(hydroxyacetyl) 5-(O-D-allosyl-3)-2,4,6-triiodo-meta-phenylene diamine 3.5-bis(glucitol)-2,4,6-triodolactoylanilide It is understood, that in referring to the sugars, it is intended to include both the cyclic and acyclic forms which may be present.

The compounds of this invention may be readily prepared by a plurality of steps employing trinitrobenzene or a substituted intermediate as the starting material. For the most part, the synthetic procedure will follow the following scheme.

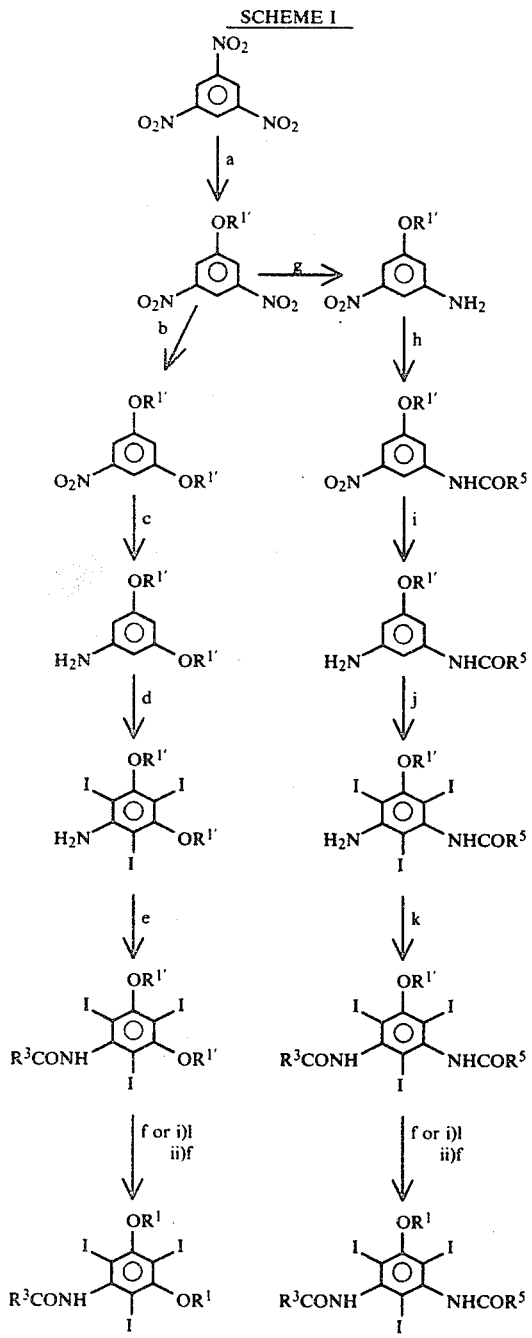

The symbols have the meaning previously described, it being understood that the two R¹s may be the same or different. The primes intend that the sugar groups may have protective groups for the hydroxyls such as iso- propylidene, methoxymethyl, etc. In some instances, reactions indicated as two steps may be performed in a single step.

a. NaH, DMF, protected cyclic glycoside having a free hydroxyl at other than the oxo carbonyl.

b. NaH, HMPA, protected cyclic glycoside having a free hydroxyl at other than the oxo carbonyl, which glycoside may be the same or different from the one employed in step (a).

c. Pd/C,$H_2$.

d. ICl, Glac. HOAc, MeOH.

e. $R^3$COCl, DMA.

f. TFA, $H_2O$.

g. $NaS_x$, EtOH.

h. $(R^5CO_2)O$, pyridine.

i. Al(Hg), MeOH.

j. ICl, Glac. HOAc.

k. $R^3$COCl, DMA.

l. THF/MeOH; Con. $NH_4OH$.

The products of the subject invention may be prepared by substitution of trinitrobenzene in the presence of base with an appropriately functionally blocked alditol or sugar, having an available hydroxyl group at other than oxo-carbonyl. The reaction is preferably conducted in a polar solvent, such as hexamethylphosphoramide, dimethylformamide, dimethtylacetamide, etc. and mixtures thereof, in the absence of water and in the presence of strong bases, e.g. alkali metal hydrides, at temperatures of $-10°$ to $100°$ C., usually $10°$ to $50°$ C. Suitably, one mole of sugar is first etherified and then the reaction is repeated if it is desired to obtain di(sugar ether) substituted benzenes.

The remaining nitro group(s) may then be reduced by conventional means, such as catalytic, e.g. palladium/charcoal, polysulfides, or the like.

The amino groups may be acylated in accordance with conventional means, such as acyl halides and tertiary amines e.g. pyridine, acyl anhydrides, activated esters, or the like. The acylation will be conducted in a polar solvent at about $-20°$ to $80°$ C., usually $0°$ to $60°$ C. Suitable solvents include those mentioned previously; in addition to dioxane, tetrahydrofuran, dimethyl sulfoxide, and the like.

Nitrogen alkylation can occur in accordance with conventional methods, normally after acylation of the amino group, taking place in the presence of proton acceptors, for example alkali hydroxides or alkali hydrides. Conventional alkylating agents may be employed, such as alkyl sulfate esters, epoxides, diazoalkanes, or the like.

Normally, hydroxyl groups will be protected during the reactions, employing ketalizing and acetalizing reagents, e.g. acetaldehyde and acetone. The removal of these groups can be achieved readily by acidic hydrolysis, for example, trifluoroacetic acid at temperatures in the range of about $15°$ to $40°$ C. If an acyl group is employed for protection, usually a carboxylic acid of from about two to seven carbon atoms, the acyl group may be removed by hydrolysis alcoholysis or amminolysis at temperatures in the range of $40°$ to $90°$ with hydroxide, alkoxide or ammonia.

The compounds of the subject invention have one or more of the following desirable properties. The compounds have enhanced water stability as compared to polyiodo contrastmedia conventionally used, particularly in the United States, acceptable viscosity, low toxicity, good compatibility when injected, high iodine concentration, low osmotic pressure, low degree of interference in the microcirculation, readily dispersible, where not sufficiently soluble, as an oil dispersion in water, and have a convenient and efficient synthetic procedure.

When employed as X-ray contrast media, they will normally be employed in combination with a pharmaceutically acceptable carrier, wherein the contrast medium compound will be present in concentrations of about 20–500 mg I/ml, more usually 100–400 mg I/ml. The quantity of contrast agent to be administered is preferably such as to stay in the system only for about two to three hours, although both shorter and longer residence periods are normally acceptable.

Besides use as contrast media, the subject compounds because of their high molecular weight and density, may find uses for a variety of other purposes. The subject compounds can be used in biological techniques, where cells are handled in solutions of high specific gravity, for example, in centrifugation or differential flotation, since their low osmolality reduces the osmotic lysis of the cells as compared to ionic compounds. In addition, the subject compounds can be used to provide density gradients for molecular weight separation by centrifugation or the like; can be prepared with radioactive iodine to be used as radioactive markers, or may be used to label compounds with iodine as radioactive labels, fluorescent quenchers, or the like, the labeling employing the oxo-carbonyl functionality of the sugar residue.

The following examples are offered by way of illustration and not by way of limitation.

EXPERIMENTAL (All temperatures not otherwise indicated are in centigrade. All parts not otherwise indicated are by weight, except for mixtures of liquids which are by volume. The following abbreviations are employed: DMF-N,N-dimethyl formamide; HMPA-hexamethylphosphortriamide; DMA-N,N-dimethyl acetamide; TFA-trifluoroacetic acid.)

EXAMPLE I 1-(O-1,2-5,6-diisopropylidene-D-glucofuranos-3-yl)-3,5-dinitrobenzene (IIIb).

To an ice-cooled, stirred suspension of sodium hydride (1.58 g, 66 mmole) in DMF (5 ml) protected with a CaCl$_2$ drying table, was added a solution of 1,2:5,6-diisopropylidene-D-glucofuranose (IIa) (17.5 g, 66 mmole) in DMF (50 ml) dropwise during 15 min. After 30 min., a solution of trinitrobenzene (Ib) (14.0 g, 66 mmole) in DMF (30 ml) was added dropwise during 10 min. The reaction mixture was now kept at 50° for 5 hr. and then at room temperature overnight. The reaction mixture was diluted with water (800 ml) and extracted with carbon tetrachloride (4×300 ml). The combined organic layers were washed with water (7×400 ml) and brine (2×100 ml) and dried. Solvent removal gave a yellow foam (25.4 g) which was crystallized from hot methanol to obtain the product (IIIb) as a crystalline solid (20.4 g, 73% yield), m.p. 120°–22°.

EXAMPLE II 1-(O-1,2:4,5-diisopropylidene-D-fructopyranos-3-yl)-3,5-dinitrobenzene (IIIc).

To an ice-cold stirred suspension of sodium hydride (1.23 g, 51.3 mmole) in HMPA (5 ml), protected with a CaCl$_2$ drying tube, was added a solution of 1,2:4,5-diisopropylidene-D-fructopyranose (IIc) (13.35 g, 51.4 mmole) in HMPA (;b 20 ml). After 2 hr, a solution of trinitrobenzene (Ib) (10.94 g, 50.0 mmole) in HMPA (60 ml) was added dropwise. The reaction mixture was left at room temperature overnight, heated at 45° for 6 hr, then diluted with water (1.71) and extracted with ether (5×300 ml). The combined ether layers were washed with water (8×500 ml), with 1 N NaOH (3×100 ml) (to remove a small amount of phenol produced) with water (4×400 ml) and dried. Solvent removal gave a residue (10.13 g) which was crystallized from hot ethanol to obtain the product (IIIc) as pale yellow needles (7.81 g, 36% yield), m.p. 150°–51°.

EXAMPLE III 1,3-Bis-(O-1,2:5,6-diisopropylidene-d-glucofuranos-3-yl)-5-nitrobenzene (IVb).

To an ice-cold, stirred suspension of sodium hydride (1.02 g, 42.3 mmole) in HMPA (10 ml) was added a solution of 1,2:5,6-diisopropylidene-D-glucofuranose (IIa) (10.98 g, 42.3 mmole) in HMPA (25 ml) dropwise. After 45 min., a solution of trinintrobenzene (Ib) (9.0 g, 42.3 mmole) in HMPA (25 ml) was added dropwise and the reaction mixture was stirred at room temperature overnight and then heated at 40° for 4 hr. The reaction mixture was cooled to room temperature and added dropwise to a stirred suspension of the sodium alkoxide in HMPA, prepared as described above starting from 1,2:5,6-diisopropylidene-D-glycofuranose (IIa) (10.98 g, 42.3 mmole) and sodium hydride (1.02 g, 42.3 mmole). The resulting mixture was stirred at room temperature for 2 hr., diluted with water (500 ml) and extracted with ether (6×250 ml). The combined ether extracts were washed with water (10×500 ml) and brine (2×100 ml) and dried. Solvent removal gave an oil (35.4 g) which was crystallized from hot ethanol to obtain the product as a pale yellow crystalline solid (18.8 g, 70% yield), m.p. 166°–7°.

EXAMPLE IV 1,3-Bis-(O-1,2:5,6-diisopropylidene-D-allofuranos-3-yl)-5-nitrobenzene (IVc).

This compound was synthesized following a procedure identical to that described above for compound (IVb). Thus starting from trinitrobenzene (Ib) (2.13 g, 10 mmole), 1,2:5,6-diisopropylidene-D-allofuranose (IIb) (2×2.60 g, total 20 mmole), sodium hydride (2×0.24 g, total 20 mmole) and HMPA (similar concentrations), a crude brown residue (1.62 g) was isolated, which was purified by column chromatography over silica gel (200 g, 2.5×35 cm) using a linear gradient of benzene (1.5 l) to benzene: ethyl acetate (1:1) (1.5 l), flow rate 3 ml/min, fraction volume 18 ml. The fractions were monitored by TLC and those containing the compound were pooled to obtain the bis-ether (IVC) as white needles (1.02 g, 16% yield), m.p. 122°–24°. A sample was recrystallized from aqueous methanol for analysis. m.p. 122°–23°.

EXAMPLE V 1,3-Bis-(O-1,2:4,5-diisopropylidene-D-fructopyranos-3-yl)-5-nitrobenzene (IVd).

This compound was synthesized following a procedure identical to that used for compound (IVb). Thus, starting from trinitrobenzene (Ib) (4.0 g, 18.5 mmole), 1,2:4,5-diisopropylidene-D-fructopyranose (IIc)

(2×4.81 g, total 37.0 mmole) sodium hydride (2×0.44 g, total 37.0 mmole) and HMPA (similar concentrations) a crude product (3.2 g) was isolated, which was purified by column chromatography over silica gel (300 g, 3.5×60 cm) using a linear gradient of benzene (2.0 l) to benzene-ethyl acetate (9:1) (2.0 l), flow rate 3 ml/min, fraction volume 18 ml. The fractions containing the compound were pooled to obtain the product (IVd) as white crystals (1.8 g, 15% yield), m.p. 148°–49°. A sample was recrystallized from aqueous methanol for analysis, m.p. 148°–148.5°.

EXAMPLE VI 3,5-Bis-(O-1,2:5,6-diisopropylidene-D-glucofuranos-3-yl)-aniline (V).

A low pressure Parr hydrogenator bottle was charged with compound IVb (6.5 g, 10 mmole), ethyl acetate (60 ml) and 10% Pd/C (1.3 g) and shaken in an atmosphere of hydrogen at 3 atm. at room temperature overnight. The mixture was filtered through celite. Removal of the solvent followed by crystallization from methanol gave the product (Vb) as a crystalline solid. (6.0 g, 97% yield); m.p. 183°–4°.

EXAMPLE VII

Synthesis of 3,5-bis-(O-1,2:5,6-diisopropylidene-D-glucofuranos-3-yl)-2,4,5-triiodoaniline (VIII).

To a stirred solution of the aniline (V) (6.0 g, 9.9 mmole) in methanol (700 ml) at 50° was added 0.2 M sodium acetate-acetic acid buffer (pH 4.6) (450 ml). The pH was adjusted to 3.7 with glacial acetic acid and a 1 M solution of iodine monochloride in glacial acetic acid (30 ml, 30 mmole) was added dropwise. The reaction mixture was kept at 50° for 5 hr and then cooled in an ice bath. The pH was adjusted from 3.4 to 4.5 by the addition of 1 N NaOH. The precipitate that resulted was filtered and washed with water (3×100 ml), with saturated aqueous sodium bicarbonate (3×100 ml) and water (3×100 ml). The residue was dried and then crystallized from benzene-hexane mixtures to obtain the triiodo-product (VIII) as a tan crystalline solid (8.0 g, 82% yield). m.p. 211°–4°.

EXAMPLE VIII 3,5-Bis-(O-1,2:5,6-diisopropylidene-D-glucofuranos-3-yl)-2,4,6-triiodoacetanilide (IXa).

To a stirred, ice-cooled solution of the triiodoaniline (VIII) (8.92 g, 9.03 mmole) in DMA (10 ml) was added acetyl chloride (3.53 g, 45.0 mmole) with protection from moisture. The solution was let stand overnight at room temperature and then poured into saturated aqueous sodium bicarbonate (1 l) with cooling in ice. The precipitate was filtered under suction and washed with water (5×100 ml). The residue was dissolved in ethyl acetate (500 ml) and washed again with aqueous sodium bicarbonate (3×100 ml), water (3×100 ml), and brine (2×50 ml) and dried. Removal of the solvent gave a solid which was purified by column chromatography over silica gel (500 g, 4.5×50 cm). The column was eluted with benzene: ethyl acetate (4:1) to remove an impurity (2.28 g), which had the same $R_f$ in TLC as the starting material, but which was not acylable. This compound has not been characterized. The column was further eluted with benzene: ethanol (4:1) (2 l), flow rate 3 ml/min, fraction volume 18 ml. Those fractions that contained the product, as monitored by TLC, were combined and solvent removed to obtain the product (IXa) as an off-white crystalline solid (6.05 g, 65% yield). m.p. 257°–8°

EXAMPLE IX 3,5-Bis-(O-1,2:5,6-diisopropylidene-D-allofuranos-3-yl)-2,4,6-triiodoacetanilide (IXb).

A solution of the bis-ether (IVc) (0.67 g, 1.05 mmole) in ethyl acetate (25 ml) was subjected to catalytic hydrogenation in the presence of 10% Pd/C (0.13 g) at 3 atm. overnight. Usual work up yielded the corresponding aniline (0.7 g), which was iodinated following the procedure described above for the synthesis of compound VIII. The crude product obtained (0.99 g) was purified by silica gel column chromatography using a linear gradient of chloroform (1.5 l) to chloroform: ethyl acetate (4:1) (1.5 l). The fractions containing the triiodo product were pooled and worked up to obtain a tan foam (0.58 g), which was acetylated employing the procedure described above for the synthesis of compound (IXa). Work up as usual gave the crude acetylated product (0.37 g), which was purified by column chromatography over silica gel using a linear gradient varying from CCl$_4$: acetone (9:1) (1 l) to CCl$_4$: acetone (6:4) (1 l), flow rate 3 ml/min, fraction volume 18 ml. The fractions containing the product were pooled to obtain the product (IXb) as a white residue, 0.17 g, 17% overall yield from (IVc).

EXAMPLE X 3,5-Bis-(O-1,2:4,5-diisopropylidene-D-fructopyranos-3-yl)-2,4,6-triiodoacetanilide (IXc).

The compound was prepared by the reduction, iodination, and acetylation sequence described above for the synthesis of the compound (IXb), with the modification that no purification was carried out after iodination. Thus, starting from 1,3-bis-(O-1,2:4,5-diisopropylidene-D-fructopyranos-3-yl)-5-nitrobenzene (IVd) (1.43 g, 2.24 mmole) and carrying out the above sequence of reactions, a crude colored acetylated product (1.02 g) was isolated. This separated into two bands of equal intensity when subjected to TLC over silica gel using benzene: ethyl acetate (3:2) solvent system. UV spectra ov the extracts from these two sopts indicated that they might be the corresponding diiodo and triiodo products. The mixture was separated by a combination of column chromatography and subsequent TLC in the solvent mentioned above. In this manner, the two following products were isolated in the pure state.

The fast moving band ($R_f$ 0.42) gave rise to the symmetrical diiodo product (VIIIb) characterized as such by UV and NMR spectral data.

The slower moving band ($R_f$ 0.29) gave rise to the expected triiodo product (IXc) as a pale yellow solid. This was crystallized from chloroform-ethyl acetate-ligroin mixtures to obtain the analytical sample as white needles (0.18 g). m.p. 213°–4° (d).

EXAMPLE XI 3,5-Bis-(O-D-glucos-3-yl)-2,4,6-triiodoacetanilide (Xa).

The protected acetanilide (IXa) (6.05 g, 5.88 mmole) was dissolved in a mixture of TFA: water (9:1) (30 ml) and the solution stirred at room temperature for 2.5 hr. The solvents were removed in vacuo at 30° and the last traces of TFA removed by co-evaporation with ethanol. To the residue in water (100 ml), freshly prepared Dowex-1 OH⁻ ion exchange resin was added with stirring to bring the pH to 6.0. The resin was filtered off and the filtrates, containing the product were passed through a Diaion-HP 20 column (3.5×40 cm), which resulted in the adsorption of the product by the resin. The column was washed with water (1 l) and thereafter it was eluted with a linear gradient varying from water (1.5 l) to aqueous methanol (1:1) (1.5 l), flow rate 2 ml/min, fraction volume 15 ml. The fractions were monitored by UV. The required compound was eluted with approximately 17 to 25% aqueous methanol. The fractions containing the product were combined and removal of the solvents yielded the bis-glucos-3-yl ether (Xa) as a white powder (4.07 g, 80% yield). m.p. 227° (d).

EXAMPLE XII 3,5-Bis-(O-D-allos-3-yl)-2,4,6-triiodoacetanilide (Xb).

The deprotection of compound (IXb) was carried out as described above for the synthesis of compound (Xa). Thus starting from the protected compound (Ib) (100 mg, 0.097 mmole) and 90% aqueous TFA (2 ml), the deprotected product (Xb) was isolated as a pale yellow foam (58.5 mg, 69% yield).

EXAMPLE XIII 3,5-Bis-(O-D-fructos-3-yl)-2,4,6-triiodoacetanilide (Xc).

The deprotection of compound (IXc) was achieved as described above for the synthesis of compound (Xa). Thus starting from the protected compound (IXc) (112 mg, 0.11 mmole) and 90% aqueous TFA (2 ml), the deprotected product (Xc) was isolated as a white powder (34 mg, 36% yield).

EXAMPLE XIV

N,N'-Bis-[3,5-bis-(O-D-glucos-3-yl)-2,4,6-triiodophenyl]-adipamide (XIIIb).

To a stirred solution of the triiodoaniline (VIII) (2.1 g, 2.13 mmole) in dry DMA (5 ml) was added adipoyl chloride (0.39 g, 2.13 mmole) with cooling in ice. The reaction mixture was heated at 50° for 2 hr and then left at room temperature overnight. After 15 hr, another equivalent of the triiodoaniline (VIII) (2.1 g, 2.13 mmole) was added, the reaction mixture stirred over a period of 2 days at room temperature and, then added to ice-cold saturated aqueous sodium bicarbonate (400 ml). The resulting precipitate was suction filtered and washed with water to obtain a yellow solid (4.42 g), which was purified by column chromatography over silica gel (250 g, 2.5×40 cm) using benzene:ethyl acetate (4:1) to elute the faster moving impurities that were present. The elution was now continued with benzene:ethanol (4:1), flow rate 3 ml/min, fraction volume 20 ml. The fractions containing the product, as determined by TLC, were pooled and the solvents removed to obtain the protected dimer (XIIIa) as a pale brown foam (2.69 g, 60% yield).

This compound (XIIIa) was treated with 90% aqueous TFA (10 ml) at room temperature for 2 hr. The solvents were removed in vacuo at 30° and the residue was co-evaporated with ethanol (6×50 ml). An aqueous solution (50 ml) of the residue was brought to pH 6.0 with Dowex-1 OH⁻ ion exchange resin and the resin was filtered off. The filtrate was chromatographed over Diaion-HP 20 resin (3.5×40 cm) using a linear gradient varying from water (1.5 l) to aqueous methanol (1:1) (1.5 l). The fractions containing the product, as measured by UV, were pooled and the solvents removed to obtain the substituted adipamide (XIIIb) as a pale yellow solid [1.07 g, 47% overall yield from compound (VIII)]. m.p. 274°–5° (d).

EXAMPLE XV 3,5-Bis-(O-D-arabinos-2-yl)-2,4,6-triiodoacetanilide (XVII).

To a solution of the bis-glucosyl ether (Xa) (90.87 g, 1 mmole) in water (10 ml), cooled to 5°, was added dropwise a solution of sodium meta-periodate (0.64 g, 3 mmole) in water (10 ml) with stirring. The reaction mixture was allowed to come to room temperature and the consumption of $NaIO_4$ was monitored by iodimetric analysis. After 6 hr, the iodimetric analysis indicated that 2 equivalents of $NaIO_4$ had been consumed. The excess $NaIO_4$ was destroyed by the addition of ethylene glycol (0.2 ml, 3.5 mmole). Iodimetric analysis indicated the absence of $NaIO_4$. The reaction mixture was cooled in ice and saturated aqueous barium hydroxide was added to bring the pH from 3.7 to 9.0. Immediately, $CO_2$ was bubbled into the reaction mixture to bring the pH to 4.7. The solvent was removed at 40° in vacuo and the residue was dried by co-evaporation with ethanol (5×30 ml). The white residue was stirred with ethanol (50 ml) and the insoluble salts were filtered off. The filtrate was freed of the solvent and the residue was dissolved in water (50 ml) and heated at 95° with Dowex-50-H⊕ resin (10 ml) for 0.5 hr. The resin was filtered off and the pH of the filtrate was adjusted to 5.5 with Dowex-1-OH⁶³ resin. The resin was removed and the solution was put on a Diaion HP-20 resin (2.6×30 cm). The column was eluted with water (1 l), followed by a linear gradient varying from water (1.5 l) to 50% aqueous methanol (1.5 l), flow rate 2 ml/min, fraction volume 15 ml, monitoring by UV. The fractions containing the compound were pooled together and the solvents were removed to obtain the product (XVII) as a white powder (0.65 g, 80% yield) TLC over silica gel: $R_f$ 0.19 [chloroform:methanol (4:1)].

EXAMPLE XVI

5-Acetoxyacetylamino-1,3-bis-(O-1,2:5,6-diisopropylidene-D-glucofuranos-3-yl)-2,4,6-triiodobenzene.

3,5-Bis-(O-1,2:5,6-diisopropylidene-D-glucofuranos-3-yl)-2,4,6-triiodobenzene (3.4 g; 3.4 mmole) was dissolved in DMA (6 ml). Acetoxyacetyl chloride (2.0 ml; 18 mmole) was added to it dropwise at 0° and the reaction mixture was stirred at room temperature overnight. It was then poured into saturated aqueous sodium bicarbonate (200 ml) with stirring and the resulting precipitate was filtered under suction, washed with water and dried in vacuo. The crude product was purified by column chromatography over silica gel using a linear gradient varying from benzene to benzene:ethyl acetate (1:1). Yield: 3.06 g. m.p. 247–48(d).

EXAMPLE XVII 5-(DL-2-Acetoxypropionylamino)-1,3-bis (O-1,2:5,6-diisopropylidene-D-glucofuranos-3-yl)-2,4,6-triiodobenzene.

3,5-Bis (O-1,2:5,6-diisopropylidene-D-glucofuranos-3-yl)-aniline (5.46 g; 5.53 mmole) was dissolved in DMA (10 ml) and DL-2-acetoxypropionyl chloride (4.0 ml; 31.6 mmole) was added to it dropwise at 0° and the reaction mixture stirred at room temperature overnight.

It was then poured into 200 ml saturated aqueous sodium bicarbonate with stirring and the resulting precipitate was filtered under suction, washed with water and dried in vacuo. The crude product was purified by column chromatography over silica gel using a linear gradient varying from benzene to benzene-ethyl acetate (1:1). Yield: 3.34 g (55%). The product could be recrystallized from ethyl acetate:hexane. m.p. 251–52.

EXAMPLE XVIII

5-Hydroxyacetylamino-1,3-bis-(O-1,2:5,6-diisopropylidene-D-glucofuranos-3-yl)-2,4,6-triiodobenzene.

5-Acetoxyacetylamino-1,3-bis-(O-1,2:5,6-diisopropylidene-D-glucofuranos-3-yl)-2,4,6-triiodobenzene (2.9 g; 2.7 mmole) was dissolved in methanol (500 ml) containing 20% ammonium hydroxide. After 20 min, the solvents were removed and a solution of the residue in chloroform was washed with water. The solution was dried and removal of the solvents resulted in a residue (2.90 g) which was further deprotected without purification.

EXAMPLE XIX

5-Hydroxyacetylamino-1,3-bis (O-D-glucofuranos-3-yl)-2,4,6-triiodobenzene.

5-(Hydroxyacetylamino-1,3-bis (O-1,2:5,6-diisopropylidene-D-glucofuranos-3-yl)-2,4,6-triiodobenzene (2.90 g) was dissolved in 90% aqueous trifluoroacetic acid (10 ml) at 0°. After stirring at room temperature for 2 hr, the solvents were removed and the residue co-evaporated with water five times. A solution of the residue in water was adjusted to pH 5.0 with Dowex-1 OH$^\ominus$ resin and then purified on Diaion-HP-20 resin. The product was isolated as a white foam. 0.87 g (36%), m.p. 204°–8° (d).

EXAMPLE XX 5-(DL-2-Hydroxypropionylamino)-1,3-bis (O-1,2:5,6-diisopropylidene-D-glucofuranos-3-yl)-2,4,6-triiodobenzene.

5-(DL-2-Acetoxypropionylamino)-1,3-bis (O-1,2:5,6-diisopropylidene-D-glucofuranos-3-yl)-2,4,6-triiodobenzene (3 g; 2.7 mmole) was dissolved in methanol (500 ml) containing 20% ammonium hydroxide. After 1.5 hr, the solvents were removed and the residue dissolved in chloroform and washed in water. The solution was dried and removal of the solvent resulted in a residue (3.13 g) which was treated with trifluoroacetic acid without further purification.

EXAMPLE XXI 5-(DL-2 Hydroxypropionylamino)-1,3-bis (O-D-glucofuranos-3-yl)-2,4,6-triiodobenzene 5-(DL-2-Hydroxypropionylamino)1,3-bis (O-1,2:5,6-diisopropylidene-D-glucofuranos-3-yl)-2,4,6-triiodobenzene (3.13 g) was dissolved in 90% aqueous TFA (10 ml) at 0°. After stirring for 2 hr at room temperature the solvents were removed and the residue was evaporated with water five times. A solution of the residue in water was adjusted to pH 5.0 with Dowex-1 OH$^\ominus$ resin and then purified on Diaion-HP-20 resin. The product was isolated as a white foam. 1.76 g (57% yield) m.p. 204°–7° (d).

EXAMPLE XXII 3-(O-1:2, 5:6-Diisopropylidene-D-glucofuranos-3-yl)-5-nitroacetanilide.

A. 3-(O-1:2, 5:6-Diisopropylidene-D-glucofuranos-3-yl)-5-nitroaniline:

To a solution of 1-(O-1:2, 5:6-diisopropylidene-D-glucofuranos-3-yl)-3,5-dinitrobenzene (9.94 g, 23.4 mmole) in 300 ml boiling ethanol is added under nitrogen freshly prepared 1.0 M sodium trisulfide solution (prepared as described below) dropwise with stirring. Refluxing and stirring under nitrogen is continued for 2 hours. The reaction mixture is cooled to room temperature and filtered through celite. The filtrate was freed of the solvent to obtain the crude product as a dark red solid which is dried in vacuo at room temperature. 10.81 g of solid is obtained. This is acetylated as described below without purification.

Sodium trisulfide solution:

Dissolve sodium monosulfide monohydrate (7.01 g, 29.2 mmole) in water under nitrogen to make a 1.0 M solution; dissolve sulfur (1.87 g, 58.4 mmole) in this solution under nitrogen at 50°

B. Acetylation

Crude 3-(O-1:2, 5:6-diisopropylidene-D-glucofuranos-3-yl)-5-nitroaniline obtained above is dissolved in 60 ml freshly distilled dry pyridine and treated with freshly distilled acetic anhydride (11 ml, 116.7 mmole). The reaction mixture is stirred at room temperature for 1 hour. Water (1.68 ml, 93.3 mmole) is added and then the solvents removed. The crude product is dissolved in 400 ml benzene and the excess sodium salts from reaction (A) filtered off. The filtrate is extracted with water (200 ml×5), washed with saturated aqueous sodium chloride (200 ml), dried over magnesium sulfate and filtered. Removal of benzene results in 9.63 g of crude product which is dissolved in benzene and applied to a 700 gm E Merck silica gel 60 column prepared with benzene. The column is eluted with a linear gradient varying from benzene to benzene:ethyl acetate (1:1). Those fractions which contained the product as shown by TLC were combined and the solvents evaporated to yield a pale yellow solid (8.14 g, 13.6 mmole, 79.6%). m.p. 80°–85° (ill-defined).

EXAMPLE XXIII 3-amino-5-(O-1:2, 5:6-diisopropylidene-D-glucofuranos-3-yl)-2,4,6-triiodoacetanilide.

Preparation of aluminum amalgam:

Aluminum foil (15.9 g, 555.6 mmole) is cut into approximately 2.5 cm×2.5 cm squares and is rolled into tubes with approximately 0.5 cm diameter. These aluminum tubes are immersed in a 2% aqueous sodium hydroxide solution which is decanted after 0.5 min. The aluminum is washed with water 3 times and immersed in a 0.5% aqueous mercuric chloride solution which is decanted after 2 minutes. The formed aluminum amalgam is washed with water 3 times, 95% ethanol, then methanol and is used immediately in the following reaction.

A. 3-amino-5-(O-1:2, 5:6-diisopropylidene-D-glucofuranos-3-yl)-acetanilide.

To the freshly prepared aluminum amalgam in a 3 necked round bottomed flask is added methanol (450 ml) followed by a solution of 3-(O-1:2, 5:6-diisopropylidene-D-glucofuranos-3-yl)-5-nitroacetanilide (11.97 g, 27.3 mmole) in 100 ml methanol with stirring. The reaction is exothermic, and the reaction mixture must be also heated to keep a constant temperature at 50°. The reaction mixture is stirred for 30–45 minutes and then filtered through celite. The precipitated aluminum hydroxide is boiled in 600 ml methanol with stirring for 10 minutes and is filtered through celite. This methanol washing process is repeated 3 times. The filtrate and washings are combined and removal of methanol gives a pale yellow solid which is dried in vacuo at room temperature to obtain the crude product (10.38 g). Due to its instability the compound is immediately taken into the next reaction, B.

Acetate buffer:
Dissolve sodium acetate in water to make 0.2 M solution; add glacial acetic acid to pH 4.6.

B. Iodination 3-amino-5-(O-1:2, 5:6-diisopropylidene-D-glucofuranos-3-yl)-acetanilide (10.38 g) is dissolved in 300 ml methanol at 40° and 1150 ml of acetate buffer is added with stirring. 200 ml of glacial acetic acid is added and a 0.9 M solution of ICl in glacial acetic acid (84.8 ml, 76.3 mmole) is added dropwise. The pH of the solution drops to 3.35. The reaction mixture is stirred at 40° for 30 min and then cooled in an ice bach. The pH is adjusted under stirring to 4.4 with 4 N NaOH. The product is extracted with ethyl acetate (1 1×2). The combined ethyl acetate extracts are washed with saturated aqueous sodium bicarbonate: 1 M aqueous sodium bisulfite solution (500 ml×3) water (500 ml×4), saturated aqueous sodium chloride (500 ml×2), dried over magnesium sulfate, and then filtered. Removal of ethyl acetate results in 18.99 g of a solid which is 98% pure by TLC. Inasmuch as the purification is easier at the next step, the solid, without further purification, is acylated with the respective acyl chlorides as described below.

EXAMPLE XXIV 3,5-diacetylamino-1-(O-1:2, 5:6-diisopropylidene-D-glucofuranos-3-yl)-2,4,6-triiodobenzene:

Reagents:
(a) N,N-dimethylacetamide (DMA) is dried over calcium hydride overnight and distilled in vacuo immediately before use.
(b) Acetyl chloride is freshly distilled immediately before use.

Into a 500 ml round bottom flask, stoppered with a calcium chloride filled tube, is placed crude 3-amino-5-(O-1:2, 5:6-diisopropylidene-D-glucofuranos-3-yl)-2,4,6-triiodoacetanilide (11.80 g, 15.0 mmole) followed by DMA (55 ml) and acetyl chloride (5.5 ml, 77.0 mmole). The reaction mixture is stirred at room temperature for 16 hours and then poured into 1.5 l of a saturated aqueous sodium bicarbonate solution at 10°. The precipitate that is formed is suction filtered, washed with saturated aqueous sodium bicarbonate solution (400 ml), water 800 ml) and dissolved in ethyl acetate (2 l). The ethyl acetate solution is washed with saturated sodium bicarbonate solution (1 l, 3 times), water (2 l) and finally with saturated aqueous sodium chloride solution (1 l). Drying (MgSO4) followed by removal of the solvent yielded the crude product (10.14 g), which is dissolved in boiling ethyl acetate (200 ml) and then benzene (20 ml) is added. The precipitate which forms is recrystallized again in boiling ethyl acetate (150 ml) and benzene (20 ml). The product is suction filtered and washed with hexane and dried in vacuo at 70° to give white needles.

This first crop yielded: 3.80 g, 4.6 mmole, 30.5% m.p. 266°.

EXAMPLE XXV

3-Methoxyacetylamino-5-acetylamino-1-(O-1,2:5,6-diisopropylidene-D-glucofuranos-3-yl)-2,4,6-triiodobenzene.

This compound was prepared following the procedure described above with acetyl chloride except that the temperature was maintained at −5°. Thus starting from 3-amino-5-(O-1,2:5,6-diisopropylidene-D-glucofuranos-3-yl)-2,4,6-triiodoacetanilide (2.08; 2.5 mmole) and methoxyacetyl chloride (2.55 mmole) in DMA (20 ml), the product was isolated after silica gel column chromatography and crystallization from ethyl acetate as a white solid (0.5 g; 23% yield), m.p. 263° (d).

EXAMPLE XXVI 3-(DL-2-Acetoxypropionylamino)-5-acetylamino-1-(O-1,2:5,6-diisopropylidene-D-glucofuranos-3-yl)-2,4,6-driiodobenzene.

This compound was prepared following the procedure described above with acetyl chloride. Thus starting from 3-amino-5-(O-1,2:5,6-diisopropylidene-D-glucofuranos-3-yl)-2,4,6-triiodoacetanilide (1.88; 2.3 mmole) and DL-2-acetoxypropionyl chloride (0.9 ml; 7.1 mmole) in DMA (4 ml), the product was isolated after silica gel column chromatography and crystallization from chloroform-hexane as white needles. (0.3 g; 13% yield) m.p. 267°–8°.

EXAMPLE XXVII 3,5-bis-Acetylamino-1-(O-D-glucofuranos-3-yl)-2,4,6-triiodobenzene.

3,5-bis-Acetylamino-1-(O-1,2:5,6-diisopropylidene-D-glucofuranos-3-yl)-2,4,6-triiodobenzene (3 g; 3.6 mmole) was dissolved in 90% aqueous TFA (30 ml) at 0° and the solution stirred for 2 hr at room temperature. The solvents were removed in vacuo and the residue was co-evaporated with ethanol thrice. An aqueous solution of the residue (50 ml) was adjusted to pH 5.0 with Dowex-1 OH⊖. Purification was achieved on a Diaion-HP-20 column using a linear gradient varying from water to 50% aqueous methanol. The pure product was obtained as a white foam (2 g; yield 70%), m.p. 218°–20° (d).

EXAMPLE XXVII

3-Methoxyacetylamino-5-acetylamino-1-(O-D-glucofuranos-3-yl)-2,4,6-triiodobenzene 3-Methoxyacetylamino-5-acetylamino-1-(O-1,2:5,6-diisopropylidene-D-glucofuranos-3-yl)-2,4,6-triiodobenzene (0.29 g; 0.34 mmole) was dissolved in 90% aqueous TFA (5 ml) at 0°. The solution was stirred at room temperature for 2 hr and the solvents were removed in vacuo and the residue was co-evaporated with ethanol thrice. The aqueous solution of the residue (50 ml) was adjusted to pH 5.0 with Dowex-1 OH⊖ resin. Purification was achieved in a Diaion-HP-20 column using a linear gradient varying from water to 50% aqueous methanol. The pure product was obtained as a white foam (0.23 g; yield 87%) m.p. 185°–90° (d).

EXAMPLE XXIX 3-(DL-2-Hydroxypropionylamino)-5-acetylamino-1-(O-1,2:5,6-diisopropylidene-D-glucofuranos-3-yl)-2,4,6-triiodobenzene A solution of 3-(DL-acetoxypropionylamino)-5-acetylamino-1-(O-1,2:5,6-diisopropylidene-D-glucofuranos-3-yl)-2,4,6-triiodobenzene (0.3 g; 0.33 mmole) in anhydrous methanol (5 ml) was treated with a 0.1 N solution of sodium methoxide in methanol (0.2 ml; 0.02 mmole) at 40° overnight. The reaction mixture was diluted with water (5 ml) and neutralized with Dowex-50 H⊕ resin to pH 5.0. The resin was filtered off and the solvents were removed to obtain the product as a white solid residue. This crude product, showing a single spot in TLC, was carried into the next step without any purification.

EXAMPLE XXX 3-(DL-2'-Hydroxypropionylamino)-5-acetylamino-1-(O-D-glucofuranos-3-yl)-2,4,6-triiodobenzene 3-(DL-Hydroxypropionylamino)-5-acetylamino-1-(O-D-glucofuranos-3-yl)-2,4,6-triiodobenzene (0.365 g; 0.41 mmole) was dissolved in 90% aqueous TFA (5 ml) at 0° and then the solution was stirred at room temperature for 2 hr. The solvents were removed in vacuo and the residue was co-evaporated with ethanol thrice. An aqueous solution of the residue (50 ml) was adjusted to pH 5.0 with Dowex-1 OH⊖ resin and then applied onto a Diaion-HP-20 column. Elution with a linear gradient varying from water to 50% aqueous methanol yielded the pure product (0.36 g; 88% yield) as a white foam; m.p. 215° (d).

EXAMPLE XXXI

A.

1-(D-1,2:5,6-Diisopropylideneglucofuranos-3-yl)-3-N-methylacetylamino-5-nitrobenzene 0.465 g (9.7 mmole) of 50% NaH (suspension in oil) is washed under the exclusion of moisture twice with benzene, then made into a slurry with 5 ml of DMF, and a solution of (3.86 g; 8.81 mmole) of 3-(O-D-1,2:5,6-diisopropylideneglucofuranos-3-yl)-5-nitroacetanilide [according to Example XXII] in 20 ml of DMF is added dropwise under ice cooling. After the hydrogen evolution has stopped, (2.51 g; 17.68 mmole) of methyl iodide is added at room temperature, and the mixture is stirred for 30 minutes; the solvent is then evaporated, the residue is dissolved in 100 ml of ethyl acetate, washed three times with 100 ml of water, the organic phase is dried over MgSO4 and evaporated. Yield (3.81 g; 8.45 mmole)=88% of theory.

B.

3-(D-1,2:5,6-Diisopropylideneglucofuranos-3-yl)-5-N-methylacetylaminoaniline 12 g (36.6 mmole) of 1-(D-1,2:5,6-diisopropylideneglucofuranos-3-yl)-3-N-methylacetylamino-5-nitrobenzene, dissolved in 100 ml of methanol, is added dropwise at 50° to 450 ml of methanol containing (16 g; 0.56 mmole) of aluminum amalgam, and the mixture is stirred for 45 minutes at 50°. The aluminum hydroxide is filtered off, extracted by boiling twice with 600 ml of methanol, and the methanolic solutions are combined and evaporated.

The crude product is a pale yellow solid which is iodinated without further purification.

C.

3-(D-1,2:5,6-Diisopropylideneglucofuranos-3-yl)-5-N-methylacetylamino-2,4,6-triiodoaniline 10 g (23.7 mmole) of 3-(D-1,2:5,6-diisopropylideneglucofuranos-3-yl)-5-N-methylacetylaminoaniline is dissolved in 300 ml of methanol, warmed to 40° and then 1.15 l of 0.2 M acetate buffer and 200 ml of glacial acetic acid are added to the reaction mixture. At 40° (85 ml; 75.5 mmole) of 0.9 M ICl solution in glacial acetic acid is added dropwise. The mixture is stirred for 30 minutes, then cooled in an ice bath, and adjusted to pH 4.4 with 4 N NaOH. The reaction solution is extracted with 1 l of ethyl acetate, the ethyl acetate phase is washed with saturated aqueous bicarbonate solution, bisulfite solution, and water, dried over MgSo4, and evaporated. The crude product is a solid which is acetylated without further purification.

D.

1-Acetylamino-3-(D-1,2:5,6-diisopropylideneglucofuranos-3-yl)-5-N-methylacetylamino-2,4,6-triiodobenzene 12 g (15 mmole) of crude 3-D-1,2:5,6-diisopropylideneglucofuranos-3-yl)-5-N-methylacetylamino-2,4,6-triiodoaniline is dissolved in 55 ml of DMA, and then (6.05 g; 77 mmole) of acetyl chloride is added dropwise and the mixture is stirred for 16 hours at room temperature. The reaction solution is stirred at 10° into 1.5 l of saturated aqueous bicarbonate solution, the precipitate is vacuum-filtered, dissolved in ethyl acetate, the ethyl acetate solution is washed with bicarbonate solution and saturated sodium chloride solution, and dried over MgSO4. Evaporation of the ethyl acetate yields a solid which is purified by crystallization from ethyl acetate/benzene 10:1.

As contrast media, the subject compounds can be used for radiographic visualization for myelo- and cis-ternography, and angiography, being employed for intravasal, subarachnoid and various local applications. As previously indicated, particular compounds find wide application because of their good water slubility, low toxicity, low osmotic pressure and relatively acceptable viscosity in aqueous media as employed. Furthermore, the synthesis can be performed by highly efficient reactions using readily available reagents obtaining the products in high yield. In addition, the compounds show excellent thermal and physiological stability, retaining their chemical structure and physical characteristics during sterilization and use.

Although the foregoing invention has been described in some detail by way of illustration and example for purposes of clarity of understanding, it will be obvious that certain changes and modifications may be practiced within the scope of the appended claims.

What is claimed is:

1. Symmetrical triodobenzenes having at least one non-glycosidyl carbohydrate ether group and at least one acylated amino group, wherein the carbohydrate group is of from about three to six carbon atoms and the acylated amino group is of from about one to six carbon atoms, all of the annular carbon atoms being substituted.

2. A symmetrical triodobenzene according to claim 1, having two carbohydrate ethers of from five to six carbon atoms bonded at oxygens other than terminal oxygen.

3. A symmetrical triodobenzene according to claim 1, having two acylated amino groups, wherein said acyl groups are of from two to four carbon atoms and have from zero to three oxy substituents.

4. A compound of the formula

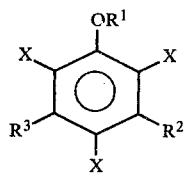

wherein:
the Xs are the same, being hydrogen or iodine;
$R^1$ is a monosaccharidic sugar residue of from about three to six carbon atoms bonded to the phenolic oxygen at other than the oxo carbonyl carbon atom;
$R^2$ is nitro, $OR^1$, wherein the two $R^1$s may be the same or different or $N(R^5)COR^4$;
$R^3$ is nitro, amino or $N(R^7)COR^6$;
$R^4$ and $R^6$ may be the same or different and are substituted or unsubstituted saturated aliphatic groups of from one to eight carbon atoms, wherein the unsubstituted group will be of from one to four carbon atoms and the substituted groups will have from zero to three oxy substituents of from zero to two carbon atoms, with the proviso that two $R^6$s on different molecules may be taken together to form a linking group, which is a bond or a divalent aliphatic linking group of from one to four carbon atoms having from zero to two oxy substituents;
$R^5$ and $R^7$ are the same or different and are hydrogen, alkyl of from one to three carbon atoms, or oxyalkyl of from two to six carbon atoms.

5. A compound according to claim 4, wherein $R^2$ is $OR^1$ and $R^3$ is $N(R^7)COR^6$.

6. A compound according to claim 4, wherein $R^2$ is $N(R^5)COR^4$.

7. A compound of the formula

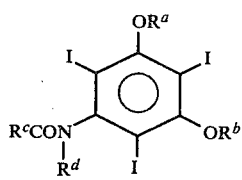

wherein:
$R^a$ and $R^b$ are monosaccharidic ethers of from about five to six carbon atoms bonded at other than the oxo carbonyl carbon atom;
$R^c$ is an alkyl group of from one to three carbon atoms or a substituted alkyl group of from one to six carbon atoms having from zero to three oxy substituents;
$R^d$ is hydrogen, alkyl of from one to two carbon atoms or oxyalkyl of from two or four carbon atoms.

8. A compound according to claim 7, wherein $R^d$ is hydrogen, $R^c$ is of from one to two carbon atoms and $R^a$ and $R^b$ are the same and are saccharides of six carbon atoms.

9. A compound according to claim 8, wherein $R^a$ and $R^b$ are glucose.

10. A compound according to claim 8, wherein $R^a$ and $R^b$ are fructose.

11. A compound according to claim 8, wherein $R^a$ and $R^b$ are allose.

12. A compound according to claim 8, wherein $R^a$ and $R^b$ are arabinose.

13. A compound of the formula

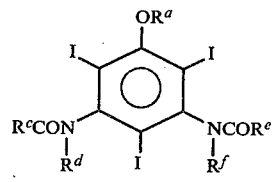

wherein $R^a$ is a monosaccharide of from about five to six carbon atoms bonded at other than the oxo carbonyl carbon atom;
$R^c$ and $R^e$ are the same or different and are unsubstituted alkyl of from one to four carbon atoms or substituted alkyl of from one to six carbon atoms having from zero to three oxy substituents;
$R^d$ and $R^f$ are the same or different and are hydrogen, alkyl of from one to two carbon atoms or oxyalkyl of from two to four carbon atoms.

14. A compound according to claim 13, wherein $R^c$ is alkyl or hydroxyalkyl of from one to three carbon atoms and $R^e$ is alkyl of from one to two carbon atoms.

15. A compound according to claim 14, wherein $R^d$ and $R^f$ are hydrogen.

16. A compound according to claim 4, wherein $R^2$ is $OR^1$ and $R^1$ is glucofuranos-3-yl and $R^3$ is acetamido.

17. A compound according to claim 4, wherein $R^2$ is $OR^1$ and $R^1$ is allofuranos-3-yl and $R^3$ is acetamido.

18. A compound according to claim 4, wherein $R^2$ is $OR^1$ and $R^1$ is fructopyranos-3-yl and $R^3$ is acetamido.

19. A compound according to claim 4, wherein $R^2$ is $OR^1$ and $R^1$ is arabinos-2-yl and $R^3$ is acetamido.

20. A compound according to claim 4, wherein $R^1$ is glucofuranos-3-yl, $R^2$ is hydroxyacetamido and $R^3$ is acetamido.

21. A compound according to claim 4, wherein $R^1$ is glucofuranos-3-yl, $R^2$ is 2-hydroxypropionamido and $R^3$ is acetamido.

22. A compound according to claim 4, wherein $R^1$ is glucofuranos-3-yl, $R^2$ is methoxyacetamido and $R^3$ is acetamido.

23. A compound according to claim 4, wherein $R^2$ is the same as $OR^1$ and is glucofuranos-3-yl and $R^3$ is 2-hydroxypropionamido.

24. An X-ray contrast medium formulation containing a sufficient amount to provide sufficient X-ray contrast of a compound according to any of claim 1, 4, 7, and 13 in a physiologically acceptable carrier.

25. A compound according to claim 4, wherein $R^2$ is $OR^1$ and $R^1$ is glycosyl.

26. A compound according to claim 25, wherein $R^3$ is methoxyacetamido.

27. A method for preparing a compound according to claim 4, which comprises:
(a) displacing from one to two nitro groups of sym-trinitrobenzene with a monosaccharidic alkoxide in a polar basic solvent at a temperature in the range of about −10° to 100° C. to form a non-glycosidic phenolic ether, wherein said alkoxide has only one oxide group at other than the oxocarbonyl position, the remaining hydroxyl groups of said monosaccharidic alkoxy being protected by oxo groups or acyl groups;

(b) reducing the remaining nitro groups to amino groups to provide aminosubstituted benzene;

(c) iodinating said amino substituted benzene to produce a sym-triiodo-aminosubstituted benzene;

(d) acylating said amino groups of said sym-triiodo-aminosubstituted benzene with an acylating agent;

(e) removing oxo protecting groups by acidic hydrolysis at a temperature in the range of about 15° to 40° C. and acyl groups by hydrolysis, alcoholysis or aminolysis at a temperature in the range of about 40° to 90° C.

* * * * *